United States Patent [19]
Collins et al.

[11] Patent Number: 5,633,282
[45] Date of Patent: May 27, 1997

[54] INHIBITION OF VIRAL INFECTION

[75] Inventors: Mary K. L. Collins; Farzin Farzaneh, both of London; Sydney Shall, Lewes; Manoochehr Tavassoli, Furze Hill, all of England

[73] Assignee: British Technology Group Limited, London, England

[21] Appl. No.: 303,203

[22] Filed: Sep. 8, 1994

Related U.S. Application Data

[63] Continuation of Ser. No. 955,721, Dec. 21, 1992, abandoned.

[30] Foreign Application Priority Data

May 25, 1990 [GB] United Kingdom ............ 9011833

[51] Int. Cl.⁶ .................. A61K 31/165; A61K 31/47
[52] U.S. Cl. .................. 514/622; 514/309; 514/616; 514/619
[58] Field of Search ................ 514/622, 309, 514/616, 619

[56] References Cited

U.S. PATENT DOCUMENTS 5,482,975  1/1996  Kun et al. ..................... 514/619

FOREIGN PATENT DOCUMENTS 0148725  7/1985  European Pat. Off. .

OTHER PUBLICATIONS

Déry et al. Virus Research (1986), 313–329 Possible role of ADP–ribosylation of adenovirus core proteins in virus infection.

Child et al. Virus Research (1988), 9 119–132 Inhibition of vaccinia virus replication by nicotinamide: evidence for ADP–ribosylation of viral proteins.

Farzaneh et al. Nucleic Acid Research (1988), 16 11319–11326 ADP–ribosylation is involved in the integration of foreign DNA into the mammalian cell genome.

Pandey et al. J. Ind. Chem. Soc. (1979), *LVI* 706–707 Search for new antiviral agents Part I. Synthesis of 2–phenyl–3–(alkyl–benzimidazolyl)quinazolin–4–ones.

Tseng et al. Proc. Natl. Acad. Sci. USA (1987), 84 1107–1111 Prevention of tumorigenesis of oncogene–transformed rat fibroblasts with DNA site inhibitors of poly(ADP–ribose) polymerase.

*Primary Examiner*—Porfirio Nazario-Gonzalez
*Assistant Examiner*—Barbara S. Frazier
*Attorney, Agent, or Firm*—Nixon & Vanderhye

[57] ABSTRACT

The use of a poly(ADP-ribose) polymerase inhibitor for the treatment of a subject against infection by a virus, in which the viral or proviral DNA integrates into the chromosome or chromosomes during its replication cycle.

13 Claims, 7 Drawing Sheets

INHIBITION OF VIRAL INFECTION

This is a continuation of application Ser. No. 07/955,721, filed 21, Dec. 1992, now abandoned.

FIELD OF THE INVENTION

The invention is in the field of the prevention of viral infection, especially (but not exclusively) retroviral infection.

DESCRIPTION OF THE PRIOR ART

Infection of cells by viruses involves receptor interaction, cell entry and uncoating of the genetic material (RNA or DNA). Some viruses (e.g. vaccinia virus) replicate without integration of viral genetic material into host cell DNA. Some DNA viruses and the retrovirus family of RNA viruses do integrate viral genetic material into infected cell DNA during the viral life cycle. In the case of retroviruses the activity of the enzyme reverse transcriptase, encoded by the retroviral pol gene converts the RNA genome into a double stranded DNA provirus in the infected cell. This provirus is then integrated into the host cell chromosomal DNA. Provirus integration into the host cell genome involves a coordinated set of DNA strand breakage and ligation events. This process requires the function of a virus-encoded protein called IN, which has both endonuclease and DNA ligase activities. However, although IN is both necessary and sufficient for provirus integration in a model system, in the absence of, as yet unidentified cell-encoded factors, this process is relatively inefficient. Therefore, high efficiency viral infection requires both the viral IN protein and cellular components. The integrated proviral DNA is then transcribed by the host cell machinery to produce RNAs which serve both as new viral genomes and mRNA.

It is necessary to develop methods of preventing retroviral infection, especially infection by human immunodeficiency viruses (HIV). The compounds AZT (3'-azido-2',3'-dideoxythymidine) and DDI (dideoxyinosine) which have been used in HIV treatment, inhibit retroviral infection by inhibiting reverse transcription. However these compounds are toxic. Moreover it is currently being suggested that retroviral infection needs to be treated by a combination therapy in which the virus is attacked by a number of different strategies. It is therefore desired to combat it in some other way than blocking reverse transcriptase.

Further prior art will be referred to after the summary of the invention without which its context would not be clear.

SUMMARY OF THE INVENTION

The present invention arises from the idea of preventing or hindering the integration of viral or proviral DNA into the host chromosome or chromosomes. It has now been found that the inhibitors of the known enzyme poly (ADP-ribose) polymerase, hereinafter abbreviated to p(ADP-r)p, (also known as ADP-ribosyl transferase, poly(ADP-ribose) transferase or poly(ADP-ribose) synthetase EC 2.4.2.30) will inhibit such integration and are therefore useful in the treatment of viral infections.

The mechanism by which these enzyme inhibitors prevent retroviral infection is not clear. It cannot be ruled out at this stage that factors other than those directly involved in poly(ADP-ribose) polymerase activity which contribute to the integration of pro-viral DNA are contributing to the observed effect.

The preferred inhibitors are aromatic amides of the general formula (1):

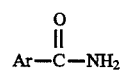

wherein Ar represents a monocyclic aromatic group, the amido group shown is bonded to a ring carbon atom of the aromatic group and Ar is unsubstituted (except by the amido group) or is substituted by at least one simple substituent atom or group compatible with the inhibitory activity.

FURTHER DESCRIPTION OF THE PRIOR ART

P(ADP-r)p is an enzyme found in the nucleus and cytoplasm of cells, requiring DNA strand breaks for its activity. Its function is post-translationally to modify proteins by poly ADP-ribosylation using $NAD^+$ as a substrate. It has also been shown to be involved in a variety of eukaryotic cellular processes which involve ligation of DNA strand breaks, possibly because it regulates DNA ligase activity.

The enzyme is known to be inhibited by several compounds (including benzamides) some of which are listed below:

1. benzamide
2. 3-aminobenzamide
3. 3-bromobenzamide
4. 3-chlorobenzamide
5. 3-fluorobenzamide
6. 3-methylbenzamide
7. 3-methoxybenzamide
8. 3-hydroxybenzamide
9. 3-N-acetylaminobenzamide (3-acetamidobenzamide)
10. 3-N-proptonylaminobenzamide (3-propionamido benzamide)
11. nicotinamide
12. 5-methyl nicotinamide
13. phthalhydrazide
14. 3-aminophthalhydrazide (Luminol or 5-amino-2,3,-dihydro-1,4,-phthalazinedione)
15. 3-nitrophthalhydrazide
16. chlorthenoxazine
17. benzoylenurea (2,4-[1H,3H] quinazolinedione)
18. thymidine Inhibitors are known to be reversible, competitive and to prevent the depletion of intracellular $NAD^+$ that is caused by DNA-damaging agents. Using these inhibitors, p(ADP-r)p has been shown to be involved in DNA excision repair (Shall S. (1984), Adv. in Rad. Biol. 11, pp. 1–69) and in the antigenic switching of Trypanosoma brucei (Cornelissen A.W.C.A. et al. (1985), Biochem. Pharm. 34, pp 4151–4156). Inhibition of nuclear p(ADP-r)p by 3-aminobenzamide was also shown to generate a large increase in spontaneous sister chromatid exchanges (Oikawa A. et al. (1980), Biochem. Biophys. Res. Commun. 97, pp 1131–1316. Lindahl-Kiessling K. & Shall S. (1987), Carcinogenesis 8, pp 1185–1188). The latter two above processes involve homologous DNA recombination. It has recently been shown that the inhibition of p(ADP-r)p by 3-methoxybenzamide or 3-aminobenzamide blocked the integration of foreign DNA into the genome during a calcium phosphate mediated DNA transfection procedure involving non-homologous/illegitimate DNA recombination (Farzaneh F. et al. (1988), Nucleic Acids Research 16, pp 11319–11326). This inhibition was shown to be specific to the integration step of DNA transfection. It was demonstrated that p(ADP-r)p activity did not influence the uptake of DNA into the cell, its episomal maintenance or replication, nor its expression either before or after integration into the host genome.

Nicotinamide, another known inhibitor of p(ADP-r)p has also been investigated. The effect of nicotinamide on vaccinia virus replication was determined by infecting monolayers of $BSC_{40}$ cells with vaccinia virus in the presence of 1–100 mM nicotinamide, and assaying the yield of progeny virions after 24 hours at 37° C. Vaccinia virus, unlike retroviruses and other DNA viruses, replicates in the cytoplasmic compartment of cells (Child, S. J. et al. (1988), Virus Research 9, pp 119–132). At concentrations of 20 mm, viral replication was affected and at 60 mM was decreased by greater than 99%. Although nicotinamide is a known inhibitor of p(ADP-r)p, the role of this nuclear enzyme in the virus replication cycle was not discussed and the concentrations of nicotinamide used (20–60 mM) would be highly toxic to the cells. 20 mM nicotinamide would rapidly exhaust the cells' supply of ATP (typically 2–3 mM). In view of this, this reference would not have been seriously considered.

Some p(ADP-r)p inhibitors have found a role in cancer therapy. DNA damage such as strand breaks, base damage and crosslinking due to X-ray or bleomycin exposure during radio or chemotherapy is reparable. The p(ADP-r)p inhibitors 3-aminobenzamide and nicotinamide were shown to inhibit recovery by delaying the rejoining of DNA.

The inhibition of integration of foreign DNA into cells by using inhibitors of p(ADP-r)p was not suspected to apply to viruses. Retroviruses and some DNA viruses (unlike vaccinia virus) integrate into the host cell chromosomal DNA during the replication cycle.

DESCRIPTION OF PREFERRED EMBODIMENTS

Figure 1:
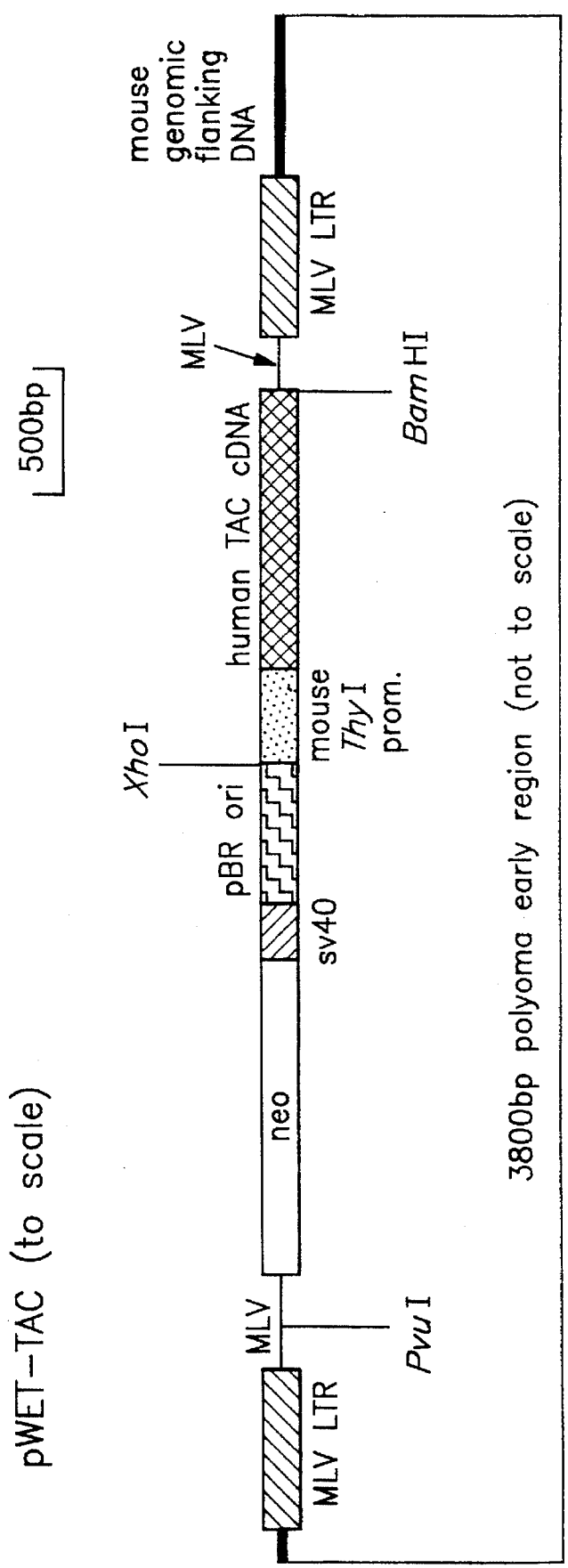
FIG. 1 shows the construction of a retroviral vector "pWeT-TAC ψ2" used for infecting cells in order to test the inhibitors.

The invention is applicable to all the viruses whose infection cycle involves the integration of the viral or proviral DNA into the host cell chromosome or chromosomes. The preferred virus type is the retrovirus. Retroviruses are RNA viruses whose life cycle involves integration of viral genetic material into host cell chromosomes. Retroviruses are classified into B, C and D-type oncoviruses (such as mouse mammary tumour virus (B), murine leukaemia virus (C), Mason Pfizer monkey virus (D)), lentiviruses (such as HIV) and foamy viruses (such as Simian foamy virus). In the case of the classical B, C and D-type oncoviruses, proviral DNA is integrated into infected cell DNA and little unintegrated proviral DNA is observed. HIV proviruses are also integrated in infected cell DNA; in this case, unintegrated proviral DNA is also detected. It is believed however that integration of HIV is necessary for a sustained infection in vivo.

The enzyme inhibitors are those which are known to inhibit p(ADP-r)P activity, but are those non-toxic inhibitors which have an inhibitor constant of <25 mM, and most preferably of <10 mM, since at lower values, lower concentrations can be used. The inhibitors are aromatic amides and have the following general formula (1):

wherein Ar represents a monocyclic aromatic group. The aromatic ring is preferably 6 membered, and may contain one or more nitrogen atoms, as in a pyridine ring: (2):

a diazine ring (3):

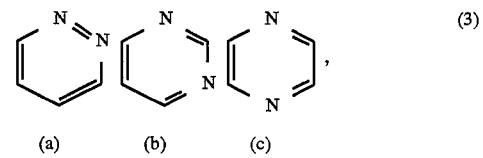

where (a) is a pyridazine ring, (b) is a pyrimidine ring and (c) is a pyrazine ring;
or a triazine ring (4):

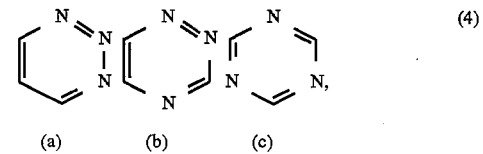

where (a) is a 1,2,3-triazine, (b) is a 1,2,4-triazine and (c) is a 1,3,5-triazine.

The amido group shown in formula (1) is bonded to a ring carbon of the aromatic group, and the Ar group is unsubstituted, except by the amido group shown, or is substituted on a ring carbon by one or more of the following substituents:

$OR^1$ wherein $R^1$ represents
    a hydrogen atom;
    an alkyl group of 1 to 4 carbon atoms unsubstituted or substituted by halogen, hydroxy or amino, or
    an acyl group (which is preferably alkylcarbonyl but could be e.g. sulphonyl) having a total chain length of up to four atoms;

a halogen atom;

a carboxy group;

a carboxymethyl group;

an alkoxycarbonyl group wherein the alkoxy group has from 1 to 4 carbon atoms;

a nitro group;

a ureido (—NHCONH$_2$) group;

an alkyl group of 1 to 4 carbon atoms as defined above for R$^1$;

an amino group of formula NR$^2$R$^3$ wherein R$^2$ and R$^3$ represent a hydrogen atom, an alkyl group having 1 to 4 carbon atoms or an alkylcarbonyl group having a total of 1 to 4 carbon atoms;

an acyl group of the formula —CO—R$^4$ where R$^4$ is an organic group preferably an alkyl group of 1 to 4 carbon atoms.

or a thio group.

It is greatly preferred, for strength of inhibitory activity, that the ring be substituted at least in the meta-position with respect to the amido group, preferably solely in the meta position.

The preferred inhibitors are those in which the Ar group is a benzenoid aromatic group, and is of the formula (5):

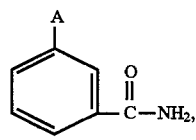

wherein A represents a hydrogen or a substituent as described above. The inhibitors which are even more preferred are those of the general formula (5) where A is NH$_2$ (3-aminobenzamide), CH$_3$O-(3-methoxybenzamide) and HCONH— (3-N-formylaminobenzamide).

The enzyme inhibitor can also be of the general formula (6):

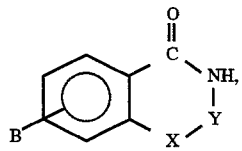

where X and Y are ring atoms or groups containing ring atoms completing a saturated ring and B represents a hydrogen atom or an amino group. X and Y may be carboxy, amino, nitrogen or oxygen groups, or an alkyl group of 1 to 4 carbon atoms which may be unsubstituted or substituted by halogen, hydroxy or amino groups. Preferably, X is —CO— and Y is —NH— or X is —NH— and Y is —CO—. This formula includes luminol (B is NH$_2$ in the 3-position relative to the hydrazide nitrogen Y is —NH— and X is —CO—), isoluminol, benzyolenurea, and chlorthenoxazine (Y is >CH—CH$_2$— CH$_2$—Cl, B is H and X is —O—).

The enzyme inhibitor can also be of the formula (7):

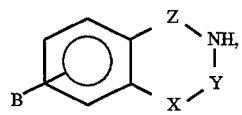

where Z is C=O or C—OH together with Z=N ring unsaturation and the ring atoms X and Y are ring atoms or groups containing ring atoms as described above completing a ring which is saturated or unsaturated. This general formula covers hydroxyquinazoline (Z is C—OH, X is —N— and Y is —CH—). B represents a hydrogen atom or an amino group.

Of all the inhibitors, 3-methoxybenzamide and 3-N-formyl-amino-benzamide are the most preferred.

The preferred route of administration is by mouth or by an injection, e.g. intravenously. When entering a high risk situation, infection would be prevented or reduced if the inhibitor is given for a period of up to 24 hours immediately before the infection by the virus. This would be the preferred method of use. Otherwise the inhibitors will be used in a method of therapy when a viral infection is diagnosed. The inhibitors can be used in concentrations of 1-5 mM per kg of body weight, but more preferably in the range 1-3 mM per kg body weight, this level being maintained in the body by repeated injection or oral doses of the inhibitor, at a frequency dependent upon the rate of clearance of the inhibitor by the body.

The following Examples illustrate the invention.

EXAMPLE 1

Effect of Poly(adp-ribose) Polymerase Inhibitors and Inhibitor Analogues on NIH-3T3 Infection by the Retroviral Vector pWET-TAC ψ2

Introduction

Retroviral vectors are composed of two parts, the actual genetic material to be transferred and the structure (the virion) which acts as the vehicle to introduce the genetic material into the cells. Beginning with the basic proviral structure, vectors are constructed wherein the majority of the sequences coding for the structural genes are deleted and replaced by the gene(s) of interest which are then transcribed under the control of the viral regulatory sequences contained in the long terminal repeat (LTR). Such recombinant retroviruses are therefore replication-defective and require packaging cell lines for the production of infectious virions. Such packaging cell lines function by providing the retroviral structural proteins which have been deleted from the retroviral vector. When transfected with an appropriate vector construct carrying a suitable packaging signal, these packaging cell line are able to release infectious virions. The virions thus released allow only a single round of infection, since the packaged vector RNA is missing one or more structural genes, no viral progeny are produced by infected cells. The retroviral vector pWeT-TAC ψ2 contains the gene neomycin phosphotransferase ("neo") which confers resistance to the drug G418. The vector is constructed as shown in FIG. 1. The BamHI-PvuI region, including the LTRs and the polyoma early region was obtained from the retroviral direction orientation vector DOL- (Korman, A. J. et al. (1987), Proc. Natl. Acad. Sci. USA, 84, pp 2150–2154). The PvuI-XhoI region including the marker gene "neo", SV40 origin and pBR origin was obtained from the pZ1P-Neo-SV(x) (Roberts, B. E. et al. (1985), J. Virol. 56, pp 403–413). The ThyI promoter together with an 0.7 kb genomic DNA fragment was described by Giguere, V. et al. (1985), EMBO J. 4, pp 2017–2024. The human TAC cDNA is a 1 kb clone described by Collins, M. K. L. (1989) Eur. J. Immunol. 19, pp 1517–1520.

(a) Infection of NIH-3T3 Cells with the Recombinant Retroviral Vector pWeT-TAC 24 hours before infection, confluent 90 mm plates of NIH-3T3 cells were trypsinized and re-plated at a density of 1×10$^5$ cells per 90 mm plate. At the time of infection, 150 recombinant virus colony forming units (previously titred by infection of NIH-3T3 cells and selection of G418-resistant colonies) and 8 μg ml$^{-1}$ polybrene (1,5-dimethyl-1,5-diazaundecamethylene polymethobromide), were added to the NIH-3T3 cells. After 72 hours, the cells were trypsinized and 1/10th of all the cells which were originally infected were plated on 90 mm plates in the presence of G418 at a final concentration of 1 mg ml$^{-1}$. The colonies were counted after a further 7 days following fixing and staining with Giemsa-methanol stain. The control number of colonies, when neither inhibitors nor inhibitor analogues were used, was 201±0, n=2.

(b) Inhibition of Infection by the Retroviral Vector pWET-TAC ψ2 by poly (ADP-ribose) Polymerase Inhibitors or Non-inhibitor Analogues NIH-3T3 cells were infected with the same titre of virus as described in (a) and 8 μg ml$^{-1}$ polybrene in the presence of one of the compounds listed in Table 1 below. The 3-substituted benzamides are inhibitors of poly(ADP-ribose) polymerase, while the 3-substituted benzoic acid and the 4-substituted benzamides are non-inhibitory analogues included for comparison.

TABLE 1

| Inhibitor/inhibitor analogue | % of control colonies counted | % inhibition achieved |
|---|---|---|
| 1. None (Control) | | |
| 2. 3 mM 4-aminobenzamide (Comparative) | 88 | 12 |
| 3. 3 mM 3-aminobenzoic acid (Comparative) | 90 | 10 |
| 4. 3 mM 3-aminobenzamide | 55 | 45 |
| 5. 1 mM 4-formylamino-benzamide (Comparative) | 92 | 8 |
| 6. 1 mM 3-N-formylamino-benzamide | 36 | 64 |
| 7. 2 mM 4-methoxybenzamide (Comparative) | 85 | 15 |
| 8. 2 mM 3-methoxybenzamide | 18 | 82 |

Following the procedure in (a), the effect of inhibitors and non-inhibitor analogues on G418 resistant colony formation was observed. The results are shown in Table 1. 3-aminobenzamide showed a significant degree of inhibition of G418-resistant colony formation, 3-N-formylaminobenzamide an even greater inhibition of infection and at only 1 mM, while 2 mM 3-methoxybenzamide was also very effective. By contrast, the non-inhibitory analogues 4-aminobenzamide, 3-amino benzoic acid, 4-formylaminobenzamide and 4-methoxybenzamide did not inhibit G418 colony formation.

The above experiment was repeated, except that the retroviral vector MPSV sup. neo (see Example 4 below) was used to infect HL-60 cells. The effect of the poly(ADP-ribose) polymerase inhibitors 5-methyl nicotinamide and chlorthenoxazine was investigated. The results are shown in Table 2 below:

TABLE 2

Effect of poly(ADP-ribose) inhibitors on the infection of HL-60 cells by the retroviral vector MPSV sup. neo.

| Inhibitor/inhibitor analogue | % of control colonies counted | % inhibition achieved |
|---|---|---|
| None (control) | | |
| 2.000 mM 5-methyl nicotinamide | 65 | 35 |
| 0.500 mM 5-methyl nicotinamide | 70 | 30 |
| 0.100 mM 5-methyl nicotinamide | 183 | +83 |
| 0.100 mM Chlorthenoxazine | 49 | 51 |

TABLE 2-continued

Effect of poly(ADP-ribose) inhibitors on the infection of HL-60 cells by the retroviral vector MPSV sup. neo.

| Inhibitor/inhibitor analogue | % of control colonies counted | % inhibition achieved |
|---|---|---|
| 0.025 mM Chlorthenoxazine | 64 | 36 |

EXAMPLE 2

Inhibition of a Previously Infected Cell Population with Poly(ADP-ribose) Polymerase Inhibitors or Non-inhibitor Analogues Introduction A control experiment was carried out in which a previously infected and selected cell population was mixed with NIH-3T3 cells and mock-infected without the retroviral vector pWET-TAC ψ2. The cell population was subject to selection for G418 resistance following treatment with the inhibitors or their analogues.

Method 24 hours before infection, confluent 90 mm (diameter) plates of NIH-3T3 cells were trypsinized and replated at a density of 1×10$^5$ cells per 90 mm plate. 75 previously infected and selected NIH-3T3 cells were mixed with these 1×10$^5$ cells. 8 mg ml$^{-1}$ polybrene was added and the cells were incubated in the presence or absence of the same compounds as in Example 1.

After 72 hours incubation, the cells were trypsinized and 1/10th of the cells were plated on a 90 mm plate, in the absence of the above compounds but in the presence of 1 mg ml$^{-1}$ G418. The colonies were counted after 7 days following fixing and staining. The control number of colonies, when neither inhibitors nor inhibitor analogues were used was 79.7; the data obtained were the mean of triplicate infections.

The results (Table 3) showed that in this situation, the enzyme inhibitors had no significant effect. Therefore, these enzyme inhibitors did not inhibit the expression of the neo gene from the viral LTR, after the proviral DNA had become integrated nor did they selectively kill infected cells.

TABLE 3

| Inhibitor/inhibitor analogue | % inhibition of control colony formation |
|---|---|
| 3 mM 4-aminobenzamide | +11 |
| 3 mM 3-aminobenzoic acid | 16 |
| 3 mM 3-aminobenzamide | +6 |
| 1 mM 4-formylaminobenzamide | +10 |
| 1 mM 3-N-formylaminobenzamide | 7 |
| 2 mM 4-methoxybenzamide | 16 |
| 2 mM 3-methoxybenzamide | 13 |

+ indicates increase of colonies rather than inhibition

EXAMPLE 3

Effect of Dose on the Inhibitor of Retroviral Infection by 3-Aminobenzamide

Proceeding as described in Example 1, but with 3-aminobenzamide as the poly (ADP-ribose) polymerase inhibitor, a small degree of inhibition of the formation of G418 resistant colonies was observed with 1 mM inhibitor, 50% at 3 mM and 60% at 5 mM.

EXAMPLE 4

Infection of NIH-3T3 and HL-60 with the Retroviral Vector MPSV.sup.28

Introduction

Figure 2:
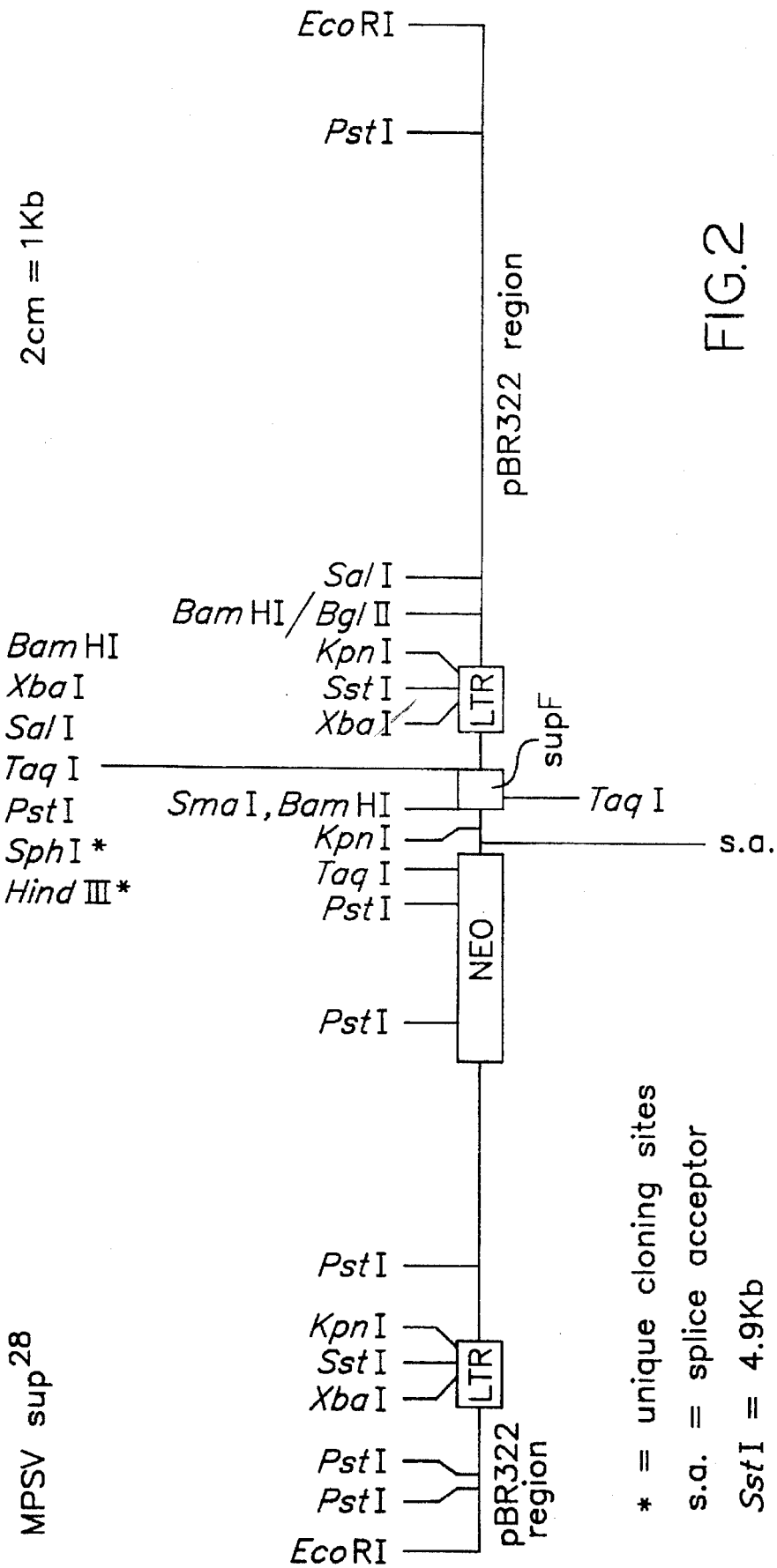
FIG. 2 shows the construction of a retroviral vector "MPSV. sup. 28". which was also used as a means of infecting cells.

MPSV.sup.28 is a recombinant retroviral vector based on the murine myeloproliferative sarcoma virus and is constructed as shown in FIG. 2. This vector carries the neomycin phosphotransferase ("neo") gene. This vector also contains the suppressor mutation supF. A suppressor mutant is a mutant which is able to overcome the effects of another. In tRNA suppressor systems, the primary mutation changes a codon in an mRNA so that the protein product is no longer functional; the secondary, suppressor mutation changes the anticodon of a tRNA, so that it recognizes the mutant codon instead of (or as well as) its original target codon. The amino acid that is now inserted restores protein function. The suppressors are named as nonsense or mis-sense, depending on the nature of the original mutation. SupF is in the former category.

In a wild-type cell, a nonsense mutation is recognized only by a release factor, terminating protein synthesis. The suppressor mutation creates an aminoacyl- tRNA that can recognize the termination codon; by inserting an amino acid, it allows protein synthesis to continue beyond the site of nonsense mutation, to synthesise a full length protein.

The effect of candidate compounds (inhibitors or non-inhibitor analogues) on infection of NIH-3T3 and HL60 cells was assayed both by counting G418 resistant colonies (following the method described in Example 1) and by Southern hybridisation analysis of high molecular weight DNA.

ANALYSIS OF THE EFFECT OF POLY(ADP-RIBOSE) POLYMERASE INHIBITORS ON RETROVIRAL INFECTION 24 hours before infection, cells were treated with 0.8% dimethylsulphoxide (DMSO) and 6 mg ml$^{-1}$ polybrene. At the time of infection, this medium was removed and replaced with fresh medium, containing the same amount of DMSO and polybrene plus $2 \times 10^5$ c.f.u. (colony forming units) of the vector either in the presence (+) or absence (−) of 2 mM 3-methoxybenzamide. Thirty sub-confluent plates of NIH/3T3 cells (15 plates with the inhibitor and 15 plates without) were infected in this way. After infection, the cells were maintained in the continuous presence or absence (+ or −) of the enzyme inhibitor for the indicated number of hours (see FIG. 4) before harvesting. Total genomic DNA was isolated from 3 plates (approximately $3 \times 10^6$ cells) for each condition (i.e. with or without the inhibitor), and digested with the restriction enzyme SstI which cuts in the two Long Terminal Repeat (LTR) sequences, releasing a 4.9 kb MPSV proviral DNA fragment containing the neomycin phosphotransferase ("neo") gene. 10mg of DNA was applied to each track on a 0.8% agarose gel. After electrophoresis, the gels were blotted onto "Gene Screen" filters and hybridised to a-$^{32}$P oligo-labelled 1.6 kb XbaI/HindIII fragment of the plasmid pM5neo containing the neo gene plus 400 bp of the MPSV virus sequences. GeneScreen (Trademark) is a nylon based membrane filter commercially available from Du Pont de Nemours (Deutschland) GmbH, NEN Division, D-6072 Dreieich, W. Germany.

Figure 4A:
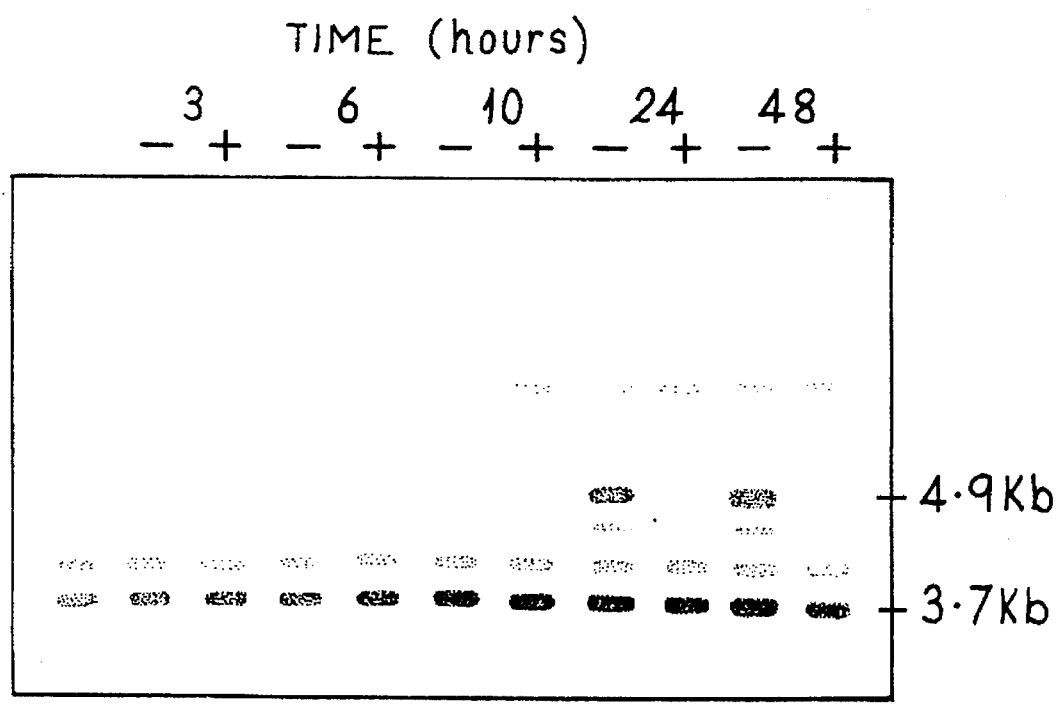
FIGS. 4a and 4b show the results of Southern hybridisation experiments of high molecular weight DNA following retroviral infection in the presence or absence of inhibitors.
Figure 4B:
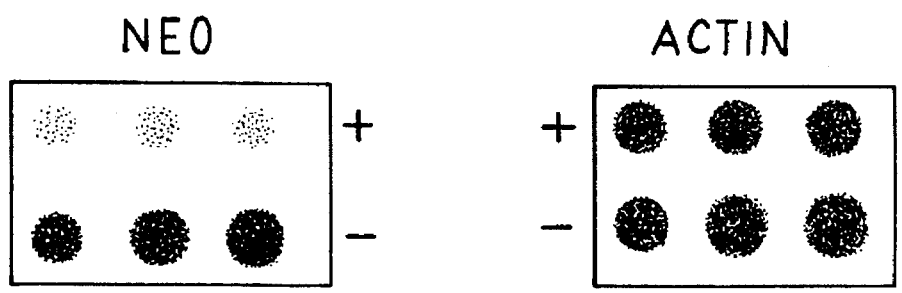

This probe hybridises to both the 4.9 kb SstI MPSV provirus fragment and a number of other endogenous proviral sequences present in the mouse genome, the most prominent of which (3.7 kb) serves as an internal control for the Southern hybridisation procedure (FIG. 4A). The presence of the 3.7 kb band in all samples (both in the presence and absence of the inhibitor) confirms that variations in the intensity of the 4.9 kb band, hybridizing to the 1.6 kb XbaI/HindIII provirus fragment is not an artefact of possible variations in the amount of DNA loaded in each track of the gel, or variations in the efficiency of DNA transfer from the gel to the GeneScreen Filter. In a control hybridisation, the filter used in FIG. 4A was stripped of the provirus probe, leaving on the filter the genomic DNA (Sambrook, J., et al. (1989), Molecular Cloning, Cold Spring Harbour Laboratory Press p14). The filter binds only single strand DNA (the precise nature of the bonding is not understood, but is thought to involve both covalent and electrostatic bonds). During the hybridisation procedure the probe binds, by hydrogen bonding, to its homologous sequence (if present) and due to its radioactive labelling it can be detected by autoradiography. The stripping procedure, breaks the hydrogen bonding between the probe and the genomic DNA sequences attached to the filter, and the probe can thus be washed away, leaving only the genomic DNA bound to the filter. The filter can then be reprobed with another radioactively labelled DNA fragment. The filter was reprobed with $^{32}$P labelled plasmid pAL41 (Alonso et al. (1986), J. Mol. Evol. 23, pp 11–22) which contains a 1.2 kb cDNA fragment of mouse a-actin. The presence of similar intensity bands in all tracks serves as a further control for the DNA loading and transfer in the Southern hybridisation procedure. The 2.3 kb SstI band hybridising to the actin probe is shown in FIG. 4B.

When in a similar experiment the filter was probed with a 762 bp PvU11 fragment from the plasmid pSV2.neo (ref. Southern P. J. and Berg P. J. (1982), J. Mol. Appl. Genet. 1, pp 327–332), containing part of the neo gene (which is carried by the MPSVsup.28 vector), but no proviral vector sequences, only the 4.9 kb MPSV band was detected.

Figure 3:
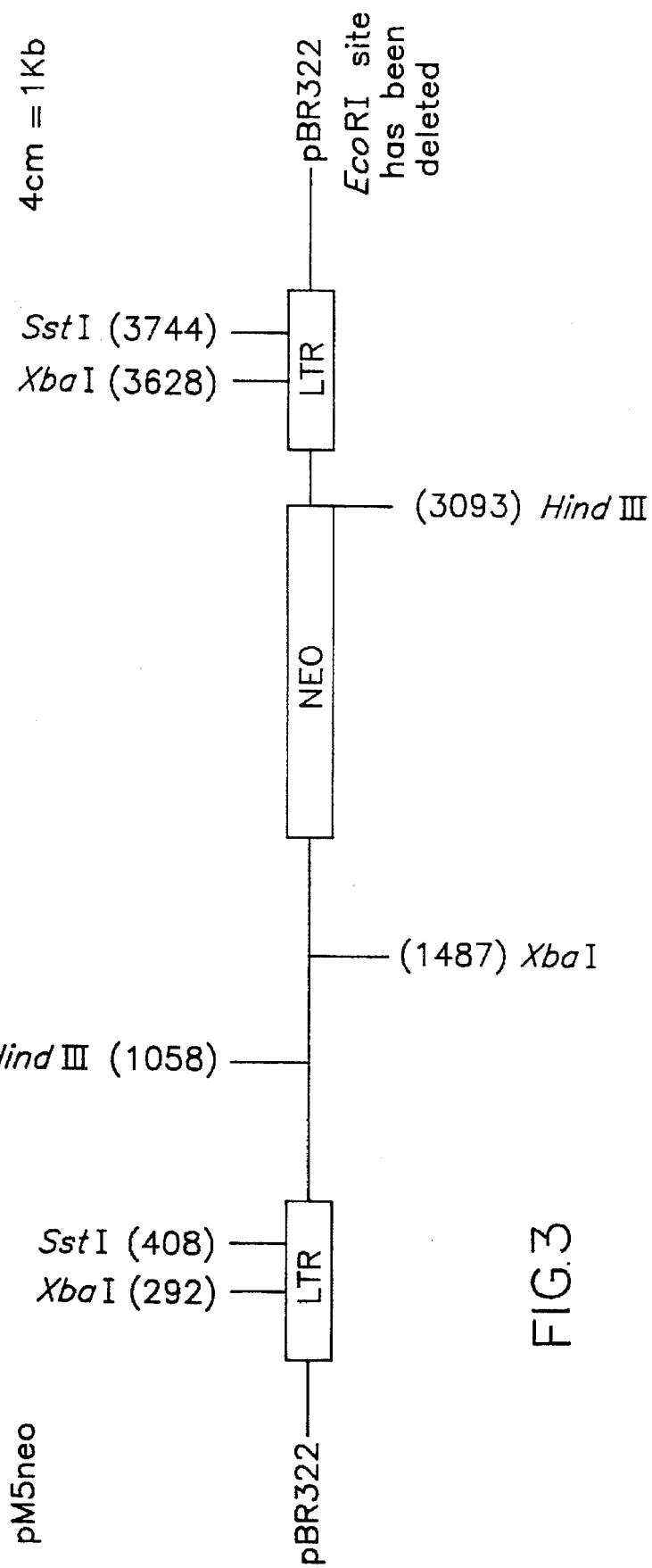
FIG. 3 shows the construction of a plasmid pM5neo used to construct a probe for a Southern hybridisation procedure to test for inhibition of incorporation of proviral DNA from the test retrovirus into chromosomes, in the presence of the inhibitors.

These results confirm the presence of viral DNA sequences only in the absence of the inhibitor (−), and that addition of the inhibitor (+) has prevented the presence of MPSVsup.28 DNA sequences in the cell genome. The construction of the plasmid pM5neo from which the XbaI/HindIII probe was prepared is shown in FIG. 3 of the drawings.

It was clear from the results that the 2 mM 3-methoxy benzamide inhibited the appearance of complete proviral DNA in the genomic DNA, this inhibition being the most obvious at 24 and 48 hours after infection.

Similar dot-blot analysis of high molecular weight DNA obtained 72 hours after infection showed clearly that 1.5 mM 3-methoxybenzamide inhibited the appearance of the proviral DNA in HL-60 cells, (FIG. 4C). In this case cells were pretreated with 0.4% DMSO and 6 mg polybrene for 24 hours. At the time of infection this medium was removed and fresh medium containing the same concentration of DMSO and polybrene, plus $5 \times 10^5$ c.f.u. of the vector were added to $10^7$ cells either in the presence (+) or absence (−) of the inhibitor ($5 \times 10^6$ cells for each condition). 24 hours after infection the medium was removed and cells were placed in fresh medium containing no DMSO or polybrene. Cells were incubated in this medium for another 48 hours before being harvested (approximately $2 \times 10^7$ cells with, and $2 \times 10^7$ without the inhibitor).

EXAMPLE 5

I vitro Testing of 3-Methoxybenzamide Cellular Toxicity and Anti-HIV Activity

A) Cellular Toxicity Testing

Toxicity to a continuous human T-cell line and human peripheral blood mononuclear cells (PBMC's) was tested by adding equal volumes of 3-methoxybenzamide (dissolved at 20 mM in RPMI 1640) at two times concentration to cells at $10^6$/ml to give final drug concentrations of 3000, 300, 30, 3 and 0.3 µM in 2 ml. Viable cell counts were performed using the trypan blue exclusion technique at Day 1 and Day 5. All concentrations were set up in duplicate and controls without 3-methoxybenzamide were included. Additional estimations of drug cytotoxicity were made at the end of the fourteen day antiviral assay by visually assessing the state of the cells.

The percentage of viable cells was calculated for each concentration of 3-methoxybenzamide and particular concentrations were deemed toxic if the percentage of viable cells fell below 50% of that of the drug-free control. In the five day cultures 3-methoxybenzamide was non-toxic at 3000 µM to both a continuous human T-cell line and PBMC's. In the antiviral assay at Day 14, cells were still more than 50% viable with compound B at all concentrations. Precise counts were not made.

B) Anti-HIV Testing

In this experimental procedure 180 µl uninfected cells were incubated with 3-methoxybenzamide at concentrations of 3000, 600, 120, 24, 4.8, 0.96 and 0.19 µM for 1 hour at 37° C. in a microtitre plate. 20 µl stock HIV-1 supernatant diluted in the same tissue culture media was then added. Medium was aspirated and replaced with fresh medium (containing 3-methoxybenzamide) on Day 1 and Day 3 to remove the virus inoculum. A P24 antigen assay was performed on Day 14 using supernatants from all wells diluted 1 in 10 and comparing the increase in P24 level to that of the positive drug-free control. An AZT control was set up at concentrations of 2.4, 4.8, 0.96, 0.19, 0.38, 0.007 and 0.001 µM. All tests and controls were set up in duplicate.

The results of the P24 antigen assay are shown in FIG. 5. FIG. 5(a) shows the P24 antigen level in supernatant in Day 14 using T-cell adapted HIV-1 and a continuous human T-cell line. FIG. 5(b) shows the P24 antigen level in supernatant using monocyte adapted HIV-1 and PHA stimulated normal human PMBC's.

Two strains of HIV were tested. Virus T is a T-cell adapted strain and was tested in a continuous human T-cell line. Virus M is a monocyte adapted strain and was tested in PBMC's.

With virus T and the T-cell line 3-methoxybenzamide showed particular activity. With virus M and PBMC's 3-methoxybenzamide partially inhibited virus production at all concentrations tested. AZT inhibited virus with a good dose response with all concentrations. Therapeutic indices (TI's) have been calculated in the different systems and are shown in Tables 4 and 5. It can be seen that 3-methoxybenzamide has a high TI (>15 800) and, as the toxic limit of 3-methoxybenzamide has not been reached, it cannot be predicted what the final TI would be.

The results are shown in the following tables.

TABLE 4

Therapeutic Indices in T-Cell Line with T-virus

| Compound (µM) | Maximum non-toxic Concentration | Minimum Antiviral Concentration | Therapeutic Index |
| --- | --- | --- | --- |
| AZT | 1000.0 | 0.007 | 142 900 |
| 3-methoxy-benzamide | ≧3000.0 | 0.19 | >15 800 |

TABLE 5

Therapeutic Indices in PBMC's with M-virus

| Compound (µM) | Maximum non-toxic Concentration | Minimum Antiviral Concentration | Therapeutic Index |
| --- | --- | --- | --- |
| AZT | 1000.0 | 0.007 | 142 900 |
| 3-methoxy-benzamide | ≧3000.0 | 0.19 | >15 800* |

*partial inhibition only

From the above results it can be seen that 3-methoxybenzamide has anti-HIV activity.

EXAMPLE 6

In vitro Testing of 4-Hydroxyquinazoline and Chlorthenoxazine for Cellular Toxicity and Anti-HIV-1 Activity The compounds tested were coded A and B:

A: 4-hydroxyquinazoline

B: chlorthenoxazine

A) Cell Toxicity Assay

200 µl of each compound (dissolved in DMSO (dimethylsulphoxide) at 150 mM) was added to 1.8 ml RPMI 1640 with L-glutamine, Hepes and 10% FCS containing $10^6$ phytohaemagglutinin (PHA) stimulated peripheral blood mononuclear cells (PBMC) in a twenty-four well tissue culture plate. Serial ten-fold dilutions were then made in RPMI containing cells to a total of five different concentrations giving 1.8 ml of cells and compound in each well in duplicate. A similar assay was set up with a continuous human T-cell line. Concentrations tested were 150, 15, 1.5, 0.15, and 0.015 µM.

Viable counts were performed using the trypan blue exclusion at Days 1, 6 and 10.

Compounds A and B were non-toxic at 150 µM to PBMC's and a continuous human T-cell line. The AZT control was non-toxic to both cell types at 150 µM.

B) Antiviral Assay

PMBC's and a continuous monocyte line were prepared at $2.0 \times 10^6$ cells/ml. Due to technical problems, the same continuous cell line as used in the toxicity assays was not used. The monocyte line and the PBMC's were unaffected, whereas all the T-cell lines were severely compromised. However, it has been shown in published literature that if a compound is not toxic to T-cells then it will not be toxic for monocyte cells. Thus the toxicity data carried out in T-cells were compatible with anti-HIV assays carried out in monocytes and PBMC's and it was thus justified to compare them for the purposes of this Example. 100 µl of each compound were added to 900 µl of this cell suspension and then diluted ten-fold in media-containing cells to give a total of five different drug concentrations as for the toxicity assay.

After incubating for thirty minutes at 37° C. HIV-1 was added to a finished concentration of approximately 1 in 10. A monocyte adapted laboratory strain was used with the monocyte line and an AZT resistant clinical isolate was used with PBMC's. Cell-free virus was washed off after a further 5 hour incubation at 37° C. and cells were resuspended in 2.5 ml of drug-free media and incubated at 37° C. for 7 days.

200µl supernatant was removed at Day 7 and tested for p24 antigen using the Coulter ELISA assay system.

Figure 6A:
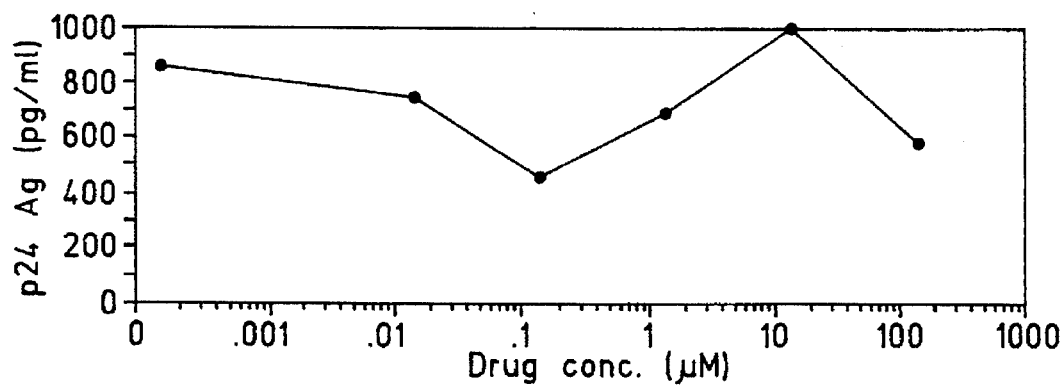
FIGS. 6a, 6b and 6c show the results of anti-HIV testing of 4-hydroxyquinazoline and chlorthenoxazine. AZT is used as a control. The tests were carried out in human peripheral blood mononuclear cells.
Figure 6B:
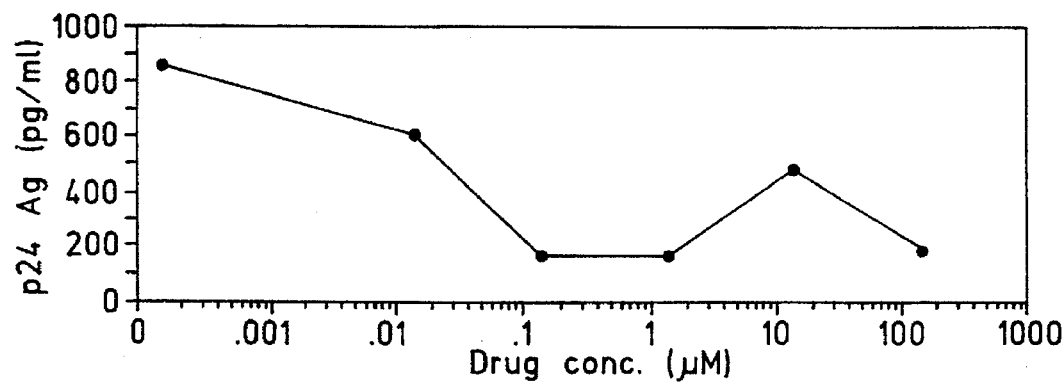
Figure 6C:
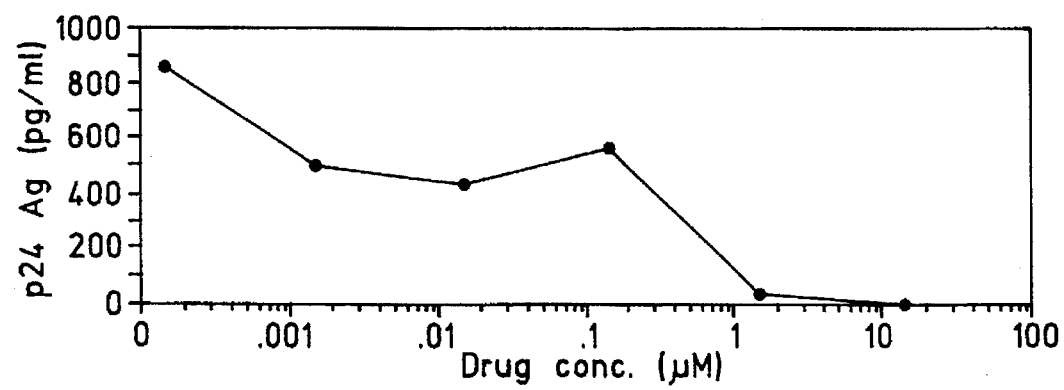
Figure 7A:
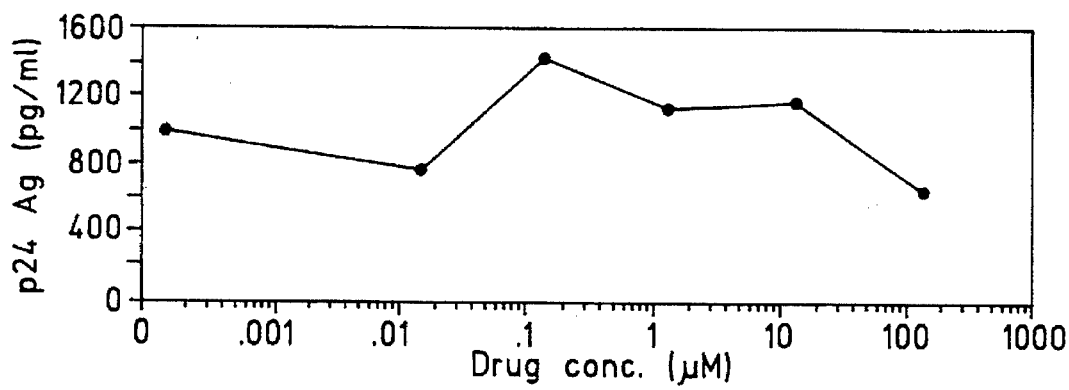
FIGS. 7a, 7b and 7c show the results of tests carried out as for FIG. 6 except that the tests were carried out in a human monocyte cell line.
Figure 7B:
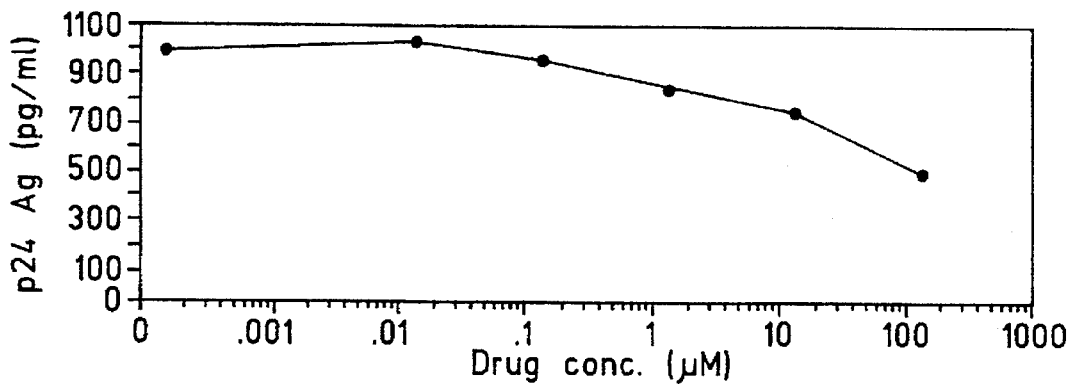
Figure 7C:
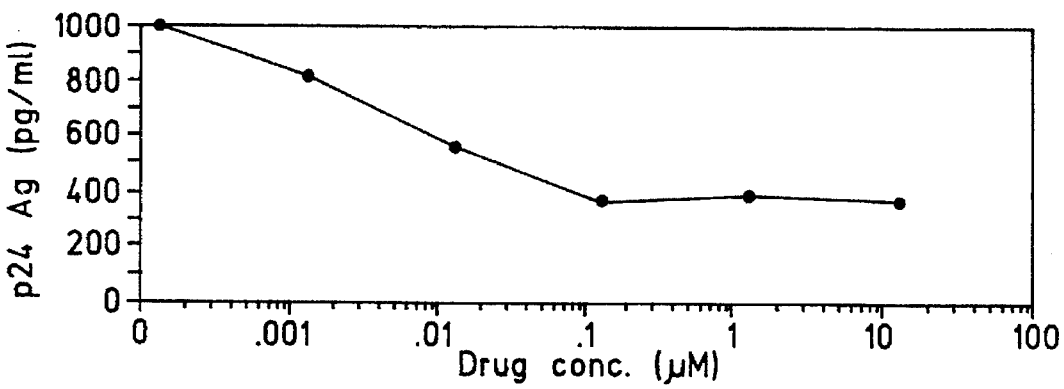
Figure 5A:
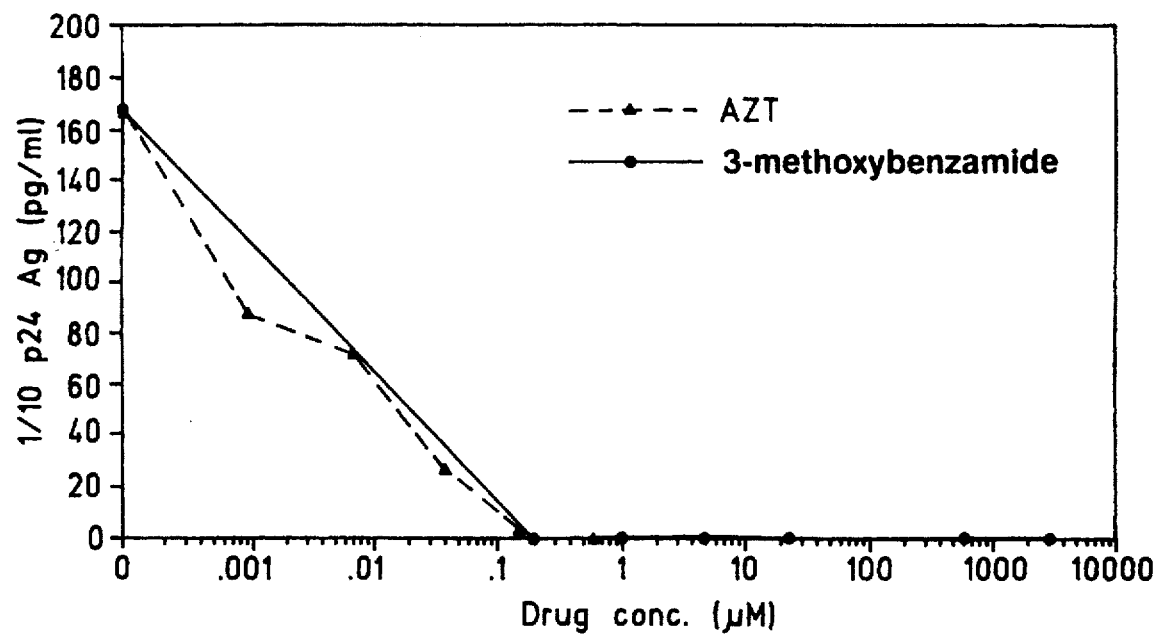
Figure 5B:
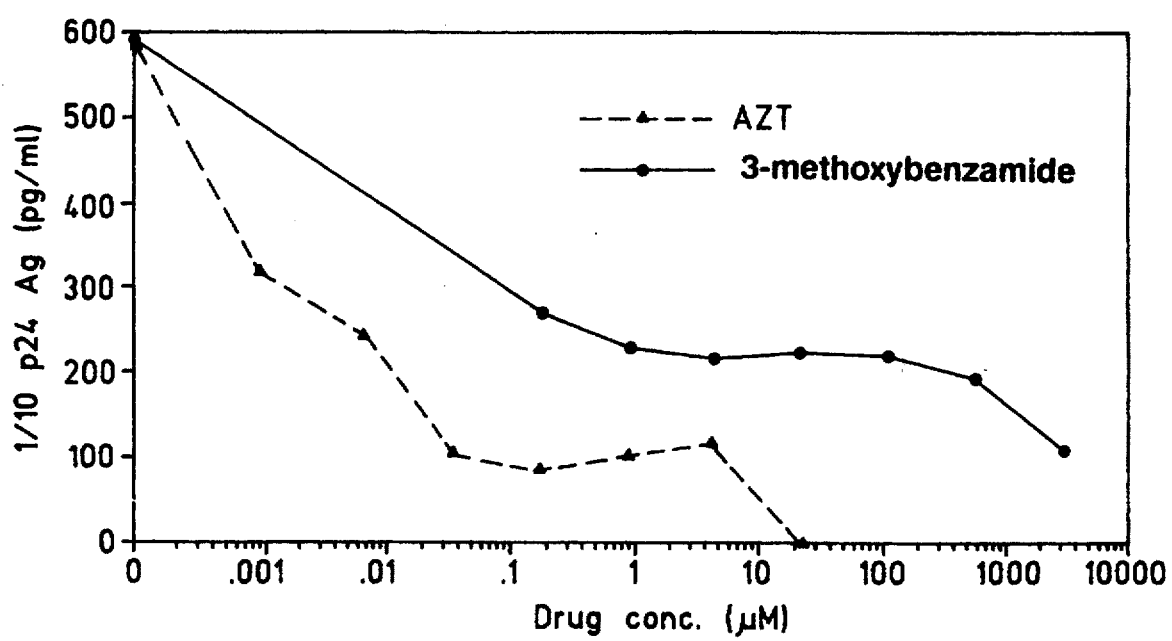

Results have been plotted as supernatant p24 antigen (pg/ml) against drug concentration at Day 7, and are shown in FIGS. 6 and 7. FIGS. 6(a), (b) and (c) show the results obtained for compounds A, B, and AZT respectively.

FIG. 6 shows the results obtained in the system using PBMC's and the AZT-resistant HIV isolate. AZT did not suppress the virus at normal inhibitory concentrations (viz. 0.015 µM), although there is a clear dose response (FIG. 6d) and the virus is inhibited completely at 1.5 µM. This isolate has an amino acid substitution at position 70 which has been demonstrated to be one of the mutations responsible for AZT resistance (Larder, B. A. and Kemp, S. (1989), Science 246, pp 1155-1158). Compound A is not active at the concentrations tested. Compound B is possibly active at 0.15 µM, but there is not a smooth dose response. Note, however, that compared to previous experiments the virus challenge had been increased approximately ten fold.

FIG. 7 shows the results obtained using the monocyte line and the laboratory strain of HIV. FIGS. 7(a), (b), and (c) show the results obtained for compounds A, B and AZT respectively. Compounds A again appear to be inactive as antiviral agents at the concentrations tested. In previous experiments the monocyte line and T-cell lines have had similar toxicity profiles against a variety of compounds and so it is justified in comparing them for the purpose of this experiment. Compound B active and has a clear dose response although the high background makes it difficult to determine the minimum antiviral concentration. The control drug, AZT, has significant antiviral activity at 0.15 µM with a clear dose response. It is possible that the cell line (monocyte/macrophase lineage) used had reduced levels of thymidine kinase, necessary for phosphorylation of AZT to its active form, which would explain why the virus inhibitory concentration is ten-fold higher than would normally be expected with a sensitive virus in a T-cell line or PBMC's. This relatively high concentration required for inhibition is consistent with the findings of another group using the same cell type (Boulerice, F. and Wainberg, M. A. (1990), Journal of Leucocyte Biology 47, pp 498-505).

Within the limitations of the assay system it would appear that compound B has potential anti-HIV activity. The toxic limit of compound A has not been reached so it cannot be said categorically that it is inactive.

The following claims define some important aspects of the invention, but do not purport to include every conceivable aspect for which protection might be sought in subsequent continuing and foreign patent applications, and should not be construed as detracting from the generality of the inventive concepts hereinbefore described.

We claim:

1. A method of treatment of a subject against a virus in which integration of viral or proviral DNA into the subject's chromosome or chromosomes is inhibited, said method comprising treating said subject with a therapeutically effective amount of an inhibitor of the enzyme poly(ADP-ribose) polymerase.

2. A method according to claim 1 wherein the virus is a retrovirus.

3. A method according to claim 2, wherein the virus is a B, C or D-type oncovirus.

4. A method according to claim 2 wherein the virus is a lentivirus.

5. A method according to claim 4 wherein the virus is a human immunodeficiency virus.

6. A method according to claim 1 where the enzyme inhibitor is an aromatic amide of the general formula (1):

wherein Ar represents a monocyclic aromatic group, the amido group shown is bonded to a ring carbon atom of the aromatic group, and Ar is unsubstituted except by the amido group shown or is substituted on a ring carbon atom by one or more of the following substituents:

$OR^1$ wherein $R^1$ represents
  a hydrogen atom;
  an alkyl group of 1 to 4 carbon atoms unsubstituted or substituted by halogen, hydroxy or amino, or
  an acyl group having a total chain length of up to four atoms;

a halogen atom;

a carboxy group;

a carboxymethyl group;

an alkoxycarbonyl group wherein the alkoxy group has from 1 to 4 carbon atoms;

a nitro group;

a ureido (—NHCONH$_2$) group;

an alkyl group of 1 to 4 carbon atoms as defined above for $R^1$;

an amino group of formula $NR^2R^3$ wherein $R^2$ and $R^3$ represent a hydrogen atom, an alkyl group having 1 to 4 carbon atoms or an alkylcarbonyl group having a total of 1 to 4 carbon atoms;

an acyl group of the formula —CO—$R^4$ where $R^4$ is an organic group preferably an alkyl group of 1 to 4 carbon atoms;

or a thio group.

7. A method according to claim 6 wherein Ar represents a benzenoid aromatic group.

8. A method according to claim 7, wherein the enzyme inhibitor is of formula (5):

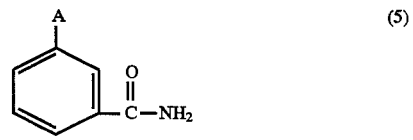

A representing a hydrogen atom or a substituent as follows:
$OR^1$ wherein $R^1$ represents
  a hydrogen atom,
  an alkyl group of 1 to 4 carbon atoms unsubstituted or substituted by halogen, hydroxy or amino, or
  an acyl group having a total chain length of up to four atoms;

a halogen atom;

a carboxy group;

a carboxymethyl group;

an alkoxycarbonyl group wherein the alkoxy group has from 1 to 4 carbon atoms;

a nitro group;

a ureido (—NHCONH$_2$) group;

an alkyl group of 1 to 4 carbon atoms as defined above for $R^1$;

an amino group of formula $NR^2R^3$ wherein $R^2$ and $R^3$ represent a hydrogen atom, an alkyl group having 1 to 4 carbon atoms or an alkylcarbonyl group having a total of 1 to 4 carbon atoms;

an acyl group of the formula —CO—R⁴ where R⁴ is an organic group;

or a thio group.

9. A method according to claim 8 where A is NH₂, CH₃O or HCONH.

10. A method according to claim 1 wherein the enzyme inhibitor is an aromatic amide of the general formula (6):

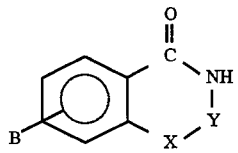 (6)

where X and Y are ring atoms completing a saturated ring and B represents a hydrogen atom or an amino group.

11. A method according to claim 10 wherein X is —CO— and Y is —NH— or X is —NH— and Y is —CO—.

12. A method according to claim 1 wherein the enzyme inhibitor is an aromatic amide of the general formula (7):

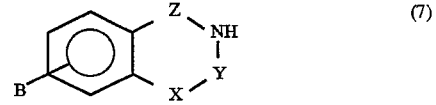 (7)

wherein Z is C=O or C—OH together with Z=N ring unsaturation and X and Y are ring atoms or groups containing ring atoms completing a saturated or unsaturated ring and B represents a hydrogen atom or an amino group.

13. A method according to claim 8, wherein R⁴ is an alkyl group of 1 to 4 carbon atoms.

* * * * *

UNITED STATES PATENT AND TRADEMARK OFFICE
CERTIFICATE OF CORRECTION

PATENT NO. : 5,633,282
DATED : May 27, 1997
INVENTOR(S) : COLLINS et al

It is certified that error appears in the above-identified patent and that said letters patent is hereby corrected as shown below:

Column 2, line 33: delete "proptonylaminobenzamide" and replace by --propionylaminobenzamide--.

Column 3, line 13: delete "mm" and replace by --mM--.

Column 10, line 31: delete "PvU11" and replace by --PvuII--;

Column 10, line 65: delete "l" and replace by --In--.

Figure 5A:
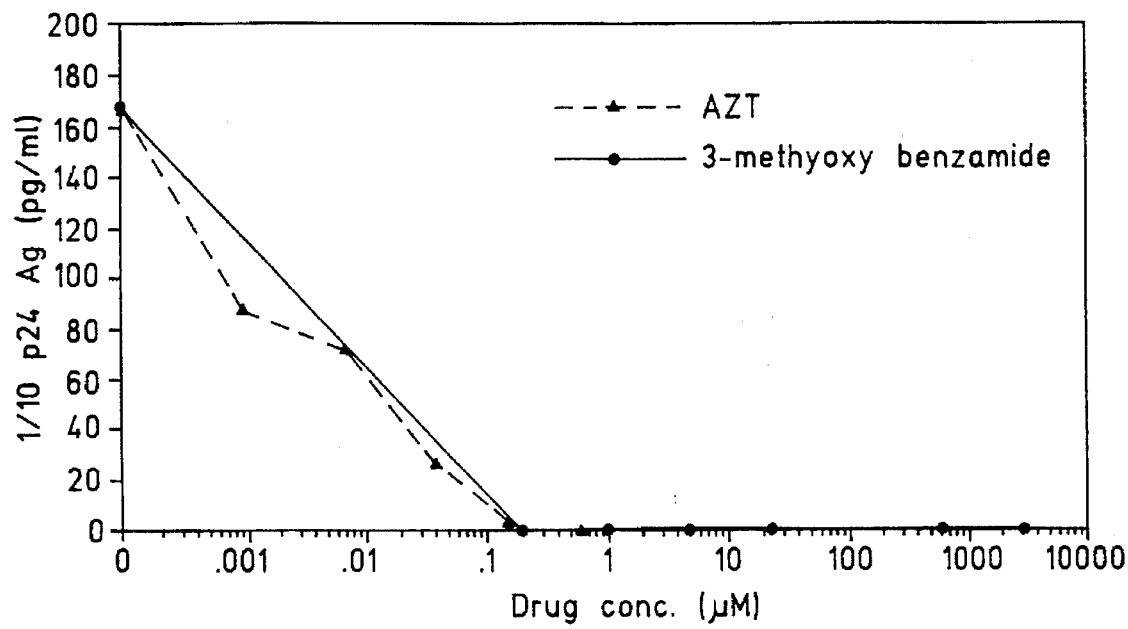
FIGS. 5a and 5b show the results of anti-HIV testing of 3-methoxy-benzamide. AZT was used as a control.

Figure 5A: cancel and replace by the Fig. 5A

Figure 5B:
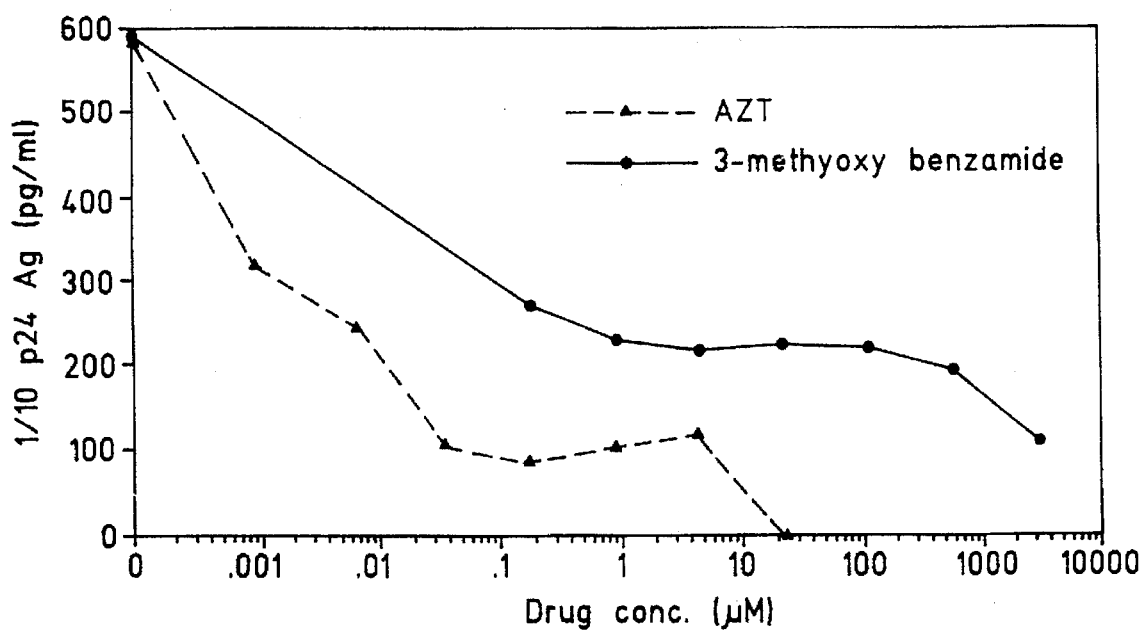

Figure 5B: cancel and replace by the Fig. 5B

Signed and Sealed this

Twenty-seventh Day of January, 1998

Attest:

BRUCE LEHMAN

Attesting Officer

Commissioner of Patents and Trademarks